United States Patent [19]

Clark

[11] 3,960,930

[45] June 1, 1976

[54] PRODUCTION OF ESTERS

[75] Inventor: Duncan Clark, Norton-on-Tees, England

[73] Assignee: Imperial Chemical Industries Limited, London, England

[22] Filed: Mar. 14, 1967

[21] Appl. No.: 622,905

[30] Foreign Application Priority Data

| Sept. 28, 1960 | United Kingdom | 33285/60 |
| Feb. 23, 1961 | United Kingdom | 6693/61 |
| Mar. 23, 1961 | United Kingdom | 10688/61 |
| Aug. 30, 1961 | United Kingdom | 31223/61 |
| Aug. 30, 1961 | United Kingdom | 31224/61 |
| July 25, 1962 | United Kingdom | 28590/62 |
| July 25, 1962 | United Kingdom | 28591/62 |

Related U.S. Application Data

[60] Division of Ser. No. 505,745, Oct. 29, 1965, abandoned, which is a continuation-in-part of Ser. Nos. 139,835, Sept. 22, 1961, abandoned, Ser. No. 139,836, Sept. 22, 1961, abandoned, Ser. No. 296,435, July 22, 1963, abandoned, and Ser. No. 296,438, July 22, 1963, abandoned.

[52] U.S. Cl............... 260/475 N; 260/410.5; 260/476 R; 260/485 N; 260/497 A; 260/604 AC

[51] Int. Cl.$^2$........................... C07C 67/05

[58] Field of Search........ 260/497 A, 476 R, 485 N, 260/475 N, 410.9

*Primary Examiner*—Robert Gerstl
*Assistant Examiner*—Michael Shippen
*Attorney, Agent, or Firm*—Cushman, Darby & Cushman

[57] ABSTRACT

The present invention relates to a process for the production of unsaturated esters which comprises the step of introducing an olefinic hydrocarbon to a solution containing a palladous salt, a carboxylic acid, carboxylate ions additional to any provided by self-ionisation of the carboxylic acid, a redox system and at most an amount of water allowing said ester formation.

6 Claims, No Drawings

PRODUCTION OF ESTERS

This is a division of copending application Ser. No. 505,745, filed Oct. 29. 1965 now abandoned, which is a continuation-in-part of co-pending U.S. Pat. applications Ser. Nos. 139,835 and 139,836 both filed 22nd Sept. 1961, now both abandoned, and Ser. Nos. 296,435 and 296,438 both filed 22nd July 1963, now both abandoned.

This invention relates to the production of unsaturated esters.

It has already been proposed to oxidise olefines such as ethylene by means of oxygen in the presence of catalysts containing palladium compounds and a metal compound which can, under the reaction conditions employed, exist in more than one degree of oxidation, for example a compound of copper or iron.

By operating in this manner and in the presence of water, Schmidt (Angewandte Chemie 71, 176–182) oxidised ethylene to acetaldehyde.

With the aim of producing vinyl esters, we attempted to carry out a similar reaction in the presence of glacial acetic acid as solvent, but no oxidation product at all was obtained by operating in this manner. We have found however that when we use as the reaction medium a solution of a carboxylio acid containing carboxylate ions we obtain an unsaturated ester.

For processes such as the oxidation of ethylene to acetaldehyde and the oxidation of olefinic hydrocarbons to unsaturated esters to be economically viable it is necessary to prevent the reduction of the palladium compound with subsequent precipitation of metallic palladium, for if this occurs the catalyst is removed from the solution and the reaction stops.

In general the precipitation of free palladium in the type of reaction described in paragraph 2 above may be prevented by reconverting it to palladous ions by reaction with the metal compound which can, under the reaction conditions employed, exist in more than one degree of oxidation. For example, if the metal is copper, reaction with cupric ions takes place according to the equation:

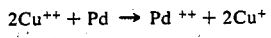

$$2Cu^{++} + Pd \rightarrow Pd^{++} + 2Cu^{+}$$

The cuprous ions formed in this way are reoxidised to cupric ions according to the equation:

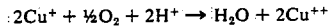

$$2Cu^{+} + \tfrac{1}{2}O_2 + 2H^{+} \rightarrow H_2O + 2Cu^{++}$$

It will be noted that water is formed by this reaction.

This reaction according to Schmidt, which is carried out in an aqueous reaction medium, is unaffected by the formation of additional water from the regeneration of the palladous salt. In our process however it would have been expected that even if the redox system which works in an aqueous medium would still, in an organic medium, retain its property of regenerating palladous ions, the water which must inevitably be formed when the redox system is regenerated would instantaneously give rise to carbonyl compounds (for example acetaldehyde when ethylene is the olefine) and thus prevent formation of unsaturated esters.

Contrary to such expectations we have found that redox systems such as cupric salts and ferric salts may be used in the substantially organic medium of our process and that unsaturated esters may be produced in good yield using such a redox system to regenerate palladous ions, even when the redox system is itself regenerated in situ with molecular oxygen.

Accordingly the invention is a process for the production of unsaturated esters which comprises the step of introducing an olefinic hydrocarbon to a solution containing a palladouus salt, a carboxylic acid, especially an aromatic or aliphatic mono- or dicarboxylic acid, carboxylate ions additional to any provided by self-ionisation of the carboxylic acid, a redox system and at most an amount of water allowing said ester formation.

Preferably molecular oxygen is also passed into the solution, either as the substantially pure gas or as air or as a mixture with an inert gas such as nitrogen or in the form of an oxygen-olefinic hydrocarbon or air-olefinic hydrocarbon mixture where the olefinic hydrocarbon is gaseous under the reaction conditions.

Particularly useful hydrocarbons in the present process are alpha olefines (i.e. olefines containing the grouping —CH=CH$_2$). The alpha olefine may be aliphatic olefine containing up to 20 carbon atoms or more, e.g. cracked wax alpha-olefins from a C$_{14}$ cut, an aryl-substituted olefine, e.g. styrene, or an unsaturated acid or ester. Preferably the aliphatic olefine contains at most 12 carbon atoms, e.g. n-hexene-1, n-octene-1 or 3:5:5-trimethyl hexene-1; more preferably at most 4 carbon atoms, e.g. ethylene, propylene or n-butene-1. Non-terminal olefines containing 4 to 8 or more carbon atoms, such as n-octene-2, may also be used in the process.

It is advantageous to keep at a minimum the time during which the olefinic hydrocarbon is in contact with the palladous salt and to ensure that, at any time, the olefinic hydrocarbon concentration in the reaction mixture is not appreciably in excess of that necessary to ensure the desired rate of reaction. A low concentration of free olefinic hydrocarbon can be ensured by adding the olefinic hydrocarbon in a stepwise manner as the reaction proceeds, rather than by introducing the whole of the olefinic hydrocarbon into the reaction system at the beginning of the reaction.

Examples of aliphatic monocarboxylic acids useful in the present process are acetic acid, propionic acid and higher acids such as n-hexanoic acid. Adipic acid is a suitable aliphatic dicarboxylic acid and benzoic and phthalic acids, especially terephthalic acid, are suitable aromatic mono- and di-carboxylic acids respectively.

The carboxylate ions employed in the process of the present invention may be derived from any aliphatic or aromatic mono- or di-carboxylic acid. They are preferably derived from one of the acids mentioned in the preceding paragraph.

It will be understood that the ester produced will correspond to either the carboxylic acid or the carboxylate ions, and in many cases both. Thus, when the process is used for the production of an acetate, either acetic acid or acetate ions must be present, and in general it is desirable to employ both. Of the carboxylate ions which may be employed, those derived from alkali metal carboxylates are the most convenient. For example, sodium, potassium and lithium carboxylates are particularly suitable for use in the present invention. The carboxylate ions may be formed in situ by, for example, the use of an alkali metal carbonate in conjunction with the carboxylic acid. When salts of dicarboxylic acids are used in the process, both di-alkali metal salts and acid salts such as potassium hydrogen phthalate are suitable sources of carboxylate ions. It is also possible to use acids and acid salts which have undergone partial esterification, for example ethyl hydrogen phthalate and ionisable salts thereof such as potassium ethyl phthalate. The use of dicarboxylate acids and/or the corresponding carboxylates results in the formation of mono-esters, di-esters, and/or mixtures thereof. Di-esters such as adipates and phthalates may be produced and such compounds are particularly suitable for use as plasticisers.

Palladous salts employed in the process of the present invention may be those of a carboxylic acid, for example palladous acetate, or inorganic salts, for example a halide. Palladous chloride, palladous bromide and mixtures thereof are the most suitable halides. It is advantageous to use, in conjunction with the palladous salt, a halide of an alkali metal, for example sodium chloride or lithium chloride, or of an alkaline earth metal, for example magnesium chloride. It is also possible to use metallic palladium initially, this being converted to a palladium salt as the reaction proceeds.

The redox system employed in the present process may be organic or inorganic in nature. For example if it is preferred to use an organic redox system, para-benzo-quinone, duroquinone, and 2-ethylanthraquinone are suitable. If, on the other hand, it is preferred to use an inorganic redox system, cupric salts are particularly suitable. For example, cupric chloride may be employed. Cupric salts of the carboxylic acid, the ester of which it is desired to produce, are also particularly suitable. Thus, in the production of vinyl acetate, cupric acetate may be used as the redox system. Other inorganic redox systems such as ferric salts, for example ferric chloride, may be used. It is also possible to employ organic and inorganic redox systems in conjunction; for example, one of the quinones named above and a cupric salt may be used conjointly. As yet another possibility, two inorganic redox systems may be used together, for example a cupric salt and a ferric salt.

As described earlier in this specification, when the process is carried out in the presence of a gas containing molecular oxygen, water is formed in the reaction zone. Although we have found than an economically viable process may be maintained, and that ester formation may take place, at a water concentration of as high as 10% by weight, it is desirable for the water content to be kept at less than 10%, for example less than 5% by weight or even less than about 1% by weight.

Steps may be taken therefore as the reaction proceeds for the removal of at least some of the water formed, thereby limiting the water content of the reaction mixture to the desired level. Water removal is facilitated by the use of a high gas rate, preferably at least 50 volumes of gas per hour per volume of reaction mixture, which tends to remove water by entrainment. Alternatively, when the olefinic hydrocarbon is a gas under the conditions of the process, e.g. propylene, it may be passed in admixture with a gas containing molecular oxygen countercurrent to a falling film of a solution containing a carboxylic acid, carboxylate ions, a palladous salt and a redox system. When the olefinic hydrocarbon is not a gas under the conditions of the process, a gas containing molecular oxygen may be passed in countercurrent flow to a falling film of a solution comprising the constituents already named together with dissolved ofefine. By carrying out the process in this way, water may be removed readily from the reaction system by vaporisation. Water may also be removed by methods such as distillation; by introducing a compound such as acetic anhydride which removes part of the water by combining with it; or by providing for the presence in the reaction system of a compound which is capable of forming an azeotrope with water; for example benzene.

Another method of minimising the effect of water, for use with olefinic hydrocarbons other than ethylene, is to carry out the reaction in two stages, the ester being produced in the first and the redox system being regenerated in the second. In this case, ester is removed in the first stage and water is removed in the second, so that contact between water, ester and olefine is minimised and the occurrence of undesirable reactions is therefore decreased.

We have also found that any deleterious effects of water may be offset by carrying out the process in the presence of one or more compounds as hereinafter defined and known for convenience as "organic polar solvents" and at the same time limiting the water content of the reaction mixture.

Thus in one form of the process according to the present invention, the reaction mixture contains less than 10% by weight of water and at least 10% by weight, based on the weight of the carboxylic acid (and preferably 5 to 95%, more preferably 5 to 80% by volume of the reaction mixture, of an organic polar solvent selected from the group consisting of urea) aliphatic carboxylic acid amides, aliphatic carboxylic acid amides substituted by at least one alkyl group on the nitrogen atom, organic nitriles, organic sulphoxides, organic sulphones and esters corresponding in the acid radical to the ester being produced. (For example, when vinyl acetate is being produced, an acetate ester such as benzyl acetate may be employed.)

Suitable organic polar solvents are acetamide; a formamide or acetamide substituted by at least one alkyl group on the nitrogen atom such as methyl acetamide, dimethylacetamide and dimethylformamide; acetonitrile; benzonitrile; dialkyl sulphoxides such as dimethyl sulphoxide; and sulpholane.

The permissible water limit depends, particularly with olefines, containing at most four carbon atoms, on the olefine partial pressure, the nature of the solvent employed and the amount of the solvent based on the amount of carboxylic acid used. Particularly for olefines containing at most four carbon atoms, the deleterious effect of water decreases with increasing pressure. The influence of the solvent:carboxylic acid weight ratio may be shown by the following consideration. In the production of vinyl acetate at atmospheric pressure using dimethylacetamide as the solvent, if the solvent:acetic acid weight ratio is 3:1, the water content, which must not exceed 10% by weight, preferably does not exceed 5% by weight. If, however, the dimethylacetamide:acetic acid weight ratio is decreased to 1:1, the water content must not exceed 7% by weight, is preferably less than 4% by weight and is more preferably less than 1% by weight.

In the present process carbonyl compounds may be formed as by-products. Thus, when using ethylene or propylene as the starting material, acetaldehyde or acetone respectively may be formed. The presence of an organic polar solvent diminishes the amount of carbonyl compound formed. Additionally, if an olefine is employed in which two different directions of attack are possible the presence of a solvent according to the present invention favours the formation of primary rather than secondary esters. This is important because primary esters are technically more useful than secondary esters.

The presence of an organic polar solvent as hereinbefore defined also diminishes the amount of di-ester formed and this is again advantageous because in general di-esters are less valuable products than mono-esters. To demonstrate this advantage, reference is made to Example 29. Ethylene and oxygen were reacted with a solution of palladous chloride as catalyst, lithium chloride, lithium acetate and cupric acetate in acetic acid at a temperature of 105°C. The ratio of the molar yields of vinyl acetate to ethylidene di-acetate was approximately 1:3. When, however, the reaction was repeated in the presence of dimethylacetamide, the weight ratio of this compound to acetic acid being 3:1, the ratio of the molar yield of vinyl acetate to ethylidene di-acetate was 34:1. From this result it is evident that the presence of dimethylacetamide substantially inhibits the formation of di-ester.

An example illustrating the improvement in the ratio of primary ester to secondary ester in the products obtained is as follows: n-Octene-1 was reacted with acetic acid and lithium acetate in the presence of palladous chloride, lithium chloride and a cupric salt, oxygen being passed continuously through the reaction mixture, which was maintained at a temperature of 100°C. The ratio of primary ester to secondary ester obtained with various organic polar solvents was as given in the Table below.

Table

| Additive | Primary Ester:Secondary Ester Ratio |
| --- | --- |
| none | 0.27 : 1 |
| benzonitrile | 0.60 : 1 |
| dimethyl sulphoxide | 1.17 : 1 |
| urea | 0.72 : 1 |

From this Table it will be seen that the addition of each of the three additives resulted in an improvement in the primary ester: secondary ester ratio, compared with that obtained in the absence of such an additive.

To show how an increase in the solvent: carboxylic acid ratio favours a high percentage of mono-ester in the product and to show how, for a fixed solvent: carboxylic acid ratio an increasing quantity of water is detrimental, reference is again made to Example 29. With the reaction system described above, results showed that with a dimethylacetamide: acetic acid ratio of 3:1 and a water content of 1.7% by weight, the product obtained contained 85% by weight of vinyl acetate (based on the total amount of vinyl acetate, acetaldehyde and ethylidene di-acetate). On decreasing the dimethyl-acetamide: acetic acid weight ratio to 1:1 and using an almost identical quantity of water (1.6% as against 1.7%), the vinyl acetate content of the product dropped to 26%, while the acetaldehyde content increased from 12.5% to 70%. Again, in the same system, using a dimethylacetamide: acetic acid weight ratio of 1:1 and a water content of 0.5% by weight, the vinyl acetate content of the product was 67% and the acetaldehyde was 33%. On increasing the water content, the amount of vinyl acetate obtained decreased while the amounts of acetaldehyde and ethylidene-diacetate increased until, with a 4.0% by weight water content, the product contained 16.5% vinyl acetate, 75.5% acetaldehyde and 8% ethylidene di-acetate.

The process of the present invention may be carried out at room temperature or at the boiling point of the reaction mixture or at any intermediate temperature. Temperatures of 50° to 180°C. are preferred, particularly 60° to 160°C., more particularly temperatures in the vicinity of 100°C.

The process may be carried out at a wide range of pressures, for example atmospheric pressure to 10 atmospheres. In particular, the use of olefine partial pressures which are greater than atmospheric is advantageous, especially when the olefine contains at most 4 carbon atoms. When using such olefins, olefine partial pressures of up to 50 atmospheres or more may be used.

The esters produced by the process of the present invention have numerous uses. Vinyl esters such as vinyl acetate, for example, are useful in the production of polymers, which in turn may be used for the production of paints.

EXAMPLE 1

Palladous chloride (50 grams), anhydrous sodium acetate (46 grams), n-octene-1 (32 grams) and glacial acetic acid (200 mls.) were mixed together and heated under reflux for 16 hours. The reaction mixture was then diluted with water, neutralised with 500 mls. of 25% caustic soda solution and the the precipitated palladium was centrifuged off. The supernatant liquid was extracted with ether. After drying over magnesium sulphate, the ether was distilled off leaving a residue of 27.9 grams of an oil. This residue was distilled and 9 fractions (including a residue) were obtained. Each fraction was analysed by infra-red spectroscopy and vapour phase chromatography. On the basis of this analysis, it was calculated that 61.5% of the olefine had undergone reaction. The product contained 11.5 grams of octenyl esters, this corresponding to a yield of 38.7% based upon the amount of olefine reacted. In the ester product, the ratio of primary to secondary ester was 1:1:2.

EXAMPLE 2

Palladous chloride (11 grams), propionic acid (43 grams) and sodium propionate (11.6 grams) were heated together with stirring until the mixture boiled under reflux. At this stage, n-octene-1 (7 grams) was added and the mixture was refluxed for a further 16 hours. The product was then centrifuged and the liquid layer was distilled under a nitrogen atmosphere. The distillate was neutralised and excess octene was separated by further distillation. The ester product remained behind as a residue and this was hydrogenated. In this way, 3.4 grams of octyl propionates were obtained, the ratio of primary to secondary product being 2:1. The amount of unchanged octene recovered was 2.9 grams so that 3.4 grams of ester had been obtained from 4.1 grams of n-octene-1, the octene conversion therefore being 59% and the yield of esters based upon the amount of octene converted being 51%.

EXAMPLE 3

Palladous chloride (53.4 grams) and acetic acid (400 mls.) wer stirred together at a temperature of 110°C. for 1 hour. Anhydrous sodium acetate (49.2 grams) was then added and heating was continued for a further 30 minutes. At the end of this period, n-hexane-1 (25.2 grams) was added dropwise. The reaction was continued for 16 hours with constant stirring, after which the product was steam distilled. The organic distillate obtained, which weighed 9.6 grams, was neutralised with sodium hydroxide and the non-aqueous layer was separated. In this way 713 grams of a clear colourless oil were obtained. This was found to contain 1.8 grams primary ester, 3.3 grams secondary ester and 0.6 gram ketone.

The residue from the steam distillation boiler was centrifuged to remove precipitated palladium, neutralised with sodium hydroxide and extracted with petroleum ether. After removing the ether by distillation a dark oil weighing 10.5 grams was obtained. This oil contained 4.1 grams primary ester, 4.8 grams secondary ester and 1.2 grams ketone. Thus, in this Example, 14 grams ester were obtained of which 5.9 grams were primary ester and 8.1 grams were secondary ester. The boiling point of this ester product was in the region of 158°C. Additionally, 1.8 grams ketone were obtained. From these results, it was calculated that the olefine conversion was 33% and that the yield of esters was 85%. The weight ratio of primary to secondary ester was 1:1.4.

EXAMPLE 4

Palladous chloride (26.7 grams), sodium acetate (24.6 grams) and acetic acid (200 mls.) were heated together at a temperature of 110°C. for a period of 30 minutes. 3:5:5-trimethylhexane-1 (16.9 grams) was added over a period of 10 minutes and heating was continued at the same temperature for 16 hours. The palladium precipitated was removed by centrifuging, and the residual liquid was neutralised and extracted with petroleum ether. The solution so obtained was dried and distilled to remove the petroleum ether. In this way, there were obtained 13.1 grams of ester, corresponding to a yield of 53%, and 0.4 gram of ketone, corresponding to a yield of 1.8%, these yields being based on the quantity of olefine fed. The olefine conversion was 54.8% and the yield of ester based on olefine converted was 97%. In the ester product, the ratio of primary to secondary esters was 2.3:1, i.e. 70% of the ester product was primary ester.

EXAMPLE 5

Palladous chloride (53.4 grams), sodium acetate (49.2 grams) and acetic acid (400 mls.) were heated together at a temperature of 110°C. for a period of 30 minutes. Alpha-olefines from a $C_{14}$ cut, weighing 53.2 grams, were added over a period of 10 minutes and the heating was continued at a temperature of 110°C. for 16 hours. The palladium precipitate was removed by centrifuging and the residual liquid was neutralised with sodium hydroxide and extracted with petroleum ether. The solution so obtained was dried and distilled to remove the petroleum ether. In this way, there were obtained 62.5 grams of product of which 45% by weight was ester. This ester had a boiling point of 142°-186°C. at a pressure of 5 mm. mercury. On analysis, this ester product was found to consist predominantly of primary unsaturated esters.

EXAMPLE 6

A solution was made up as follows:

| | |
|---|---|
| palladous chloride | 0.8 grams |
| lithium chloride | 0.56 gram |
| cupric chloride | 3.95 grams |
| potassium hydrogen phthalate | 6.56 grams |
| phthalic acid | 30.0 grams |
| n-octene-1 | 10.8 grams |

This mixture was heated to a temperature of 105°C. and oxygen was passed through at a rate of 1 liter per hour for 6 hours. At the end of this time, the product was separated, whereby 1.3 grams of olefine and 4.1 grams of ester were obtained. On analysis, this ester product was shown to consist largely of di-ester. Assuming that the product was entirely di-ester, the yield of this based on n-octene-1 reacted was approximately 25%.

EXAMPLE 7

Palladous chloride (53.4 grams) was warmed with stirring for one hour with acetic acid (400 mls.). Sodium acetate (49.2 grams) was added and the mixture was heated with stirring for a further 30 minutes. Styrene (33.6 grams) was added slowly from a dropping funnel and the reaction mixture was stirred continuously at a temperature of 110°C. for a period of 16 hours. The mixture was then allowed to cool after which it was centrifuged to remove any metallic palladium which had been precipitated. The filtrate was neutralised with a concentrated solution of sodium hydroxide and extracted with petroleum ether. Fractionation of the ethereal solution gave a dark orange-brown oil which was dried over anhydrous magnesium sulphate, filtered and weighed. The weight of the product, which was almost entirely composed of esters, was 33.3 grams, which corresponds to an ester yield based on the amount of styrene employed of 70%. On hydrogenation using a palladium catalyst, the crude ester product gave rise to a material containing a high proportion of 2-phenyl ethyl acetate, from which it may be deduced that the crude ester consisted largely of beta-phenyl vinyl acetate.

EXAMPLE 8

In this Example results were obtained using (a) a 30% volume concentration of olefine and (b) a 10% volume concentration of olefine. The comparative results show the benefit of a low olefine concentration. (a) Palladous chloride (0.264 grams), lithium chloride (0.304 gram), lithium acetate (3.307 grams), cupric chloride (1.301 grams), dimethyl-formamide (54.5 mls.), acetic acid (15.6 mls.) and n-octene-1 (30 mls.) were heated to a temperature of 110°C., oxygen being passed through at a rate of 20 liters per hour. The reaction was continued for 4 hours after which the product was separated. In this way, 9.1 grams of ester were obtained. When this material was subjected to analysis, it was found that 59% of the ester was primary, the remaining 41% being secondary. Thus, the ratio of primary to secondary was 1.44:1. The 41% of secondary was made up of 26% acetate-2, 10% acetate-3 and 5% acetate-4. (b) The same quantities of salts were employed in this part of the Example as were employed in (a) above. The other constituents were dimethylformamide, 70 mls.; acetic acid, 20 mls.; n-octene-1, 10 mls. The reaction was carried out as described in (a) above except that the total reaction time was 6 hours. A total of 5.1 grams of ester was obtained of which 90% was primary and 10% was secondary. Of this 10% of secondary ester, 6% was acetate-2 and 4% was acetate-3. The ratio of primary ester to secondary ester produced was 9:1. It will be observed that in this part of the Example, a much higher primary:secondary ratio was obtained than in (a) above, in which a much greater concentration of n-octene-1 was present.

EXAMPLE 9

A solution was made up as follows:

| | | |
|---|---|---|
| palladous chloride | 3.52 grams | $2 \times 10^{-2}$ mole |
| lithium chloride | 1.67 grams | $4 \times 10^{-2}$ mole |
| lithium acetate | 5.03 grams | $8 \times 10^{-2}$ mole |
| cupric acetate | 7.20 grams | $3 \times 10^{-2}$ mole |
| acetic acid | 200 mls. | |

This solution was raised to a temperature of 104°C. and a gas mixture comprising 30% by volume ethylene and 70% by volume oxygen was passed through it at a rate of 10 liters per hour for 8 hours. The reaction was carried out using a specially cooled reflux condenser so that substantially no water was allowed to escape from the reaction system. The reaction product on analysis was found to contain the following constituents:

| | |
|---|---|
| acetaldehyde | $14.9 \times 10^{-2}$ mole |
| ethylidene di-acetate | $0.98 \times 10^{-2}$ mole |
| vinyl acetate | $0.67 \times 10^{-2}$ mole |
| 1:2-di-acetoxyethane | $0.05 \times 10^{-2}$ mole |

It will be observed that in this Example in which substantially no water escapes from the reaction system, vinyl acetate is formed as well as a considerable amount of acetaldehyde.

EXAMPLE 10

Example 9 was repeated except that the time of reaction was 6 hours and the reflux condenser employed was water-cooled, so that some of the water formed in the reaction escaped from the system. The product obtained contained the following substances:

| | |
|---|---|
| acetaldehyde | $3.1 \times 10^{-2}$ mole |
| ethylidene di-acetate | $6.85 \times 10^{-2}$ mole |
| vinyl acetate | $0.9 \times 10^{-2}$ mole |

EXAMPLE 11

Example 10 was repeated except that the materials removed by vaporisation were substantially completely condensed and there was no re-cycle to the reaction zone. In this way, the water content of the reaction mixture was maintained at a low level. After 6 hours an analysis of the reaction product gave the following results:

| | |
|---|---|
| acetaldehyde | $2.5 \times 10^{-2}$ mole |
| ethylidene di-acetate | $3.5 \times 10^{-2}$ mole |
| vinyl acetate | $4.1 \times 10^{-2}$ mole |

EXAMPLE 12

In this Example, cupric chloride sas employed in place of cupric acetate. A solution was made up as follows:

| | |
|---|---|
| palladous chloride | 1.05 grams |
| lithium chloride | 1.00 gram |
| lithium acetate | 5.03 grams |
| cupric chloride | 4.00 grams |
| acetic acid | 200 grams |

An ethylene-oxygen mixture was passed through the reaction mixture maintained at a temperature of 108°C., reaction being carried out substantially as described in Example 10. The duration of the reaction was 140 hours, which resulted in the formation of a greater quantity of product and in consequence a more accurate determination of 1:2-di-acetoxyethane present. An analysis of the reaction mixture gave the following results:

| | |
|---|---|
| acetaldehyde | $19.95 \times 10^{-2}$ mole |
| ethylidene di-acetate | $44.4 \times 10^{-2}$ mole |
| vinyl acetate | $20.1 \times 10^{-2}$ mole |
| 1:2-di-acetoxyethane | $2.63 \times 10^{-2}$ mole |

Part of the acetaldehyde obtained in this Example was found to be in its trimeric form.

EXAMPLE 13

A solution was made up as follows:

| | | |
|---|---|---|
| palladous chloride | 3.52 grams | $2 \times 10^{-2}$ mole |
| lithium chloride | 1.67 grams | $4 \times 10^{-2}$ mole |
| sodium propionate | 7.68 grams | $8 \times 10^{-2}$ mole |
| cupric chloride | 4.05 grams | $3 \times 10^{-2}$ mole |
| propionic acid | 200 mls. | |

This solution was raised to a temperature of 120°C. and a gas mixture comprising 30% ethylene and 70% oxygen was passed through as in Example 10 at a rate of 10 liters per hour for 9 hours. At the end of this time, the product was analysed. It was found to contain:

| | |
|---|---|
| acetaldehyde | $4.1 \times 10^{-2}$ mole |
| vinyl propionate | $5.1 \times 10^{-2}$ mole |

Additionally, the product was believed to contain one or more di-propionates including some ethylidene di-propionate, but the nature and amounts of these compounds were not ascertained.

EXAMPLE 14

A solution was made up as follows:

| | Weight | Amount |
|---|---|---|
| palladous chloride | 0.352 gram | 0.002 mole |
| lithium chloride | 0.84 gram | 0.02 mole |
| lithium acetate | 13.2 grams | 0.2 mole |
| cupric acetate | 16.3 grams | 0.09 mole |
| acetic acid | 200 ml. | |

This solution was raised to a temperature of 105°C., and an oxygen-ethylene gas mixture was passed through it at atmospheric pressure for 3 hours at a rate of 10 liters per hour, the oxygen:ethylene volume ratio being 1:2. Two runs were carried out, the final water concentration in the first run being 0.1% and in the second run 1.1% of the reaction mixture by weight. The reaction products were separated and the molar percentage of vinyl acetate, acetaldehyde and ethylidene diacetate determined, based on the total yield of these three compounds. In the Table below, the product distribution for these three compounnds is given for the two different standing water concentrations.

| % by weight water | Product Distribution (moles %) | | |
|---|---|---|---|
| | vinyl acetate | acetaldehyde | ethylidene di-acetate |
| 0.1 | 57 | 14 | 29 |
| 1.1 | 30 | 30 | 40 |

EXAMPLE 15

Two solutions were made up having the following compositions:

| | Weight | Amount |
|---|---|---|
| palladous chloride | 0.352 gram | 0.002 mole |
| lithium chloride | 1.68 gram | 0.04 mole |
| lithium acetate | 66.0 grams | 1.0 mole |
| cupric acetate | 16.3 grams | 0.09 mole |
| acetic acid | 200 ml. | |

Reaction with an ethylene-oxygen mixture was carried out as described in Example 14, the final water concentrations being 0.6 and 1.0% respectively. The results obtained for product distribution are summarised in the Table below:

| % by weight water | Product Distribution (moles %) | | |
|---|---|---|---|
| | vinyl acetate | acetaldehyde | ethylidene di-acetate |
| 0.6 | 73 | 19 | 8 |
| 1.0 | 60 | 25 | 15 |

EXAMPLE 16

A solution was made up as follows:

| | | |
|---|---|---|
| palladous chloride | 0.352 gram | $2 \times 10^{-3}$ mole |
| lithium chloride | 0.167 gram | $4 \times 10^{-3}$ mole |
| lithium acetate | 5.03 grams | $8 \times 10^{-2}$ mole |
| cupric acetate | 7.2 grams | $3 \times 10^{-2}$ mole |
| acetic acid | 200 mls. | |

This solution was raised to a temperature of 104°C. and a gas mixture comprising 30% by volume ethylene and 70% by volume oxygen was passed through it for a period of 5.2 hours. The reaction was carried out as described in Example 10. The analysis of the reaction product showed that the following compounds were present:

| | |
|---|---|
| acetaldehyde | $0.30 \times 10^{-2}$ mole |
| vinyl acetate | $0.95 \times 10^{-2}$ mole |
| ethylidene di-acetate | $0.37 \times 10^{-2}$ mole |

EXAMPLE 17

Example 16 was repeated except that the reaction time was 25 hours and the temperature was 115°–118°C. On analysis, the product was found to contain the following constituent:

| | |
|---|---|
| acetaldehyde | $1.49 \times 10^{-2}$ mole |
| vinyl acetate | $5.01 \times 10^{-2}$ mole |
| ethylidene di-acetate | $1.51 \times 10^{-2}$ mole |

A comparison of these results with those given in the previous Example shows that the use of a longer reaction time gives a greater output of products. This indicates the continuous nature of the present process.

EXAMPLE 18

A solution comprising the following components was prepared:

| | |
|---|---|
| anhydrous lithium acetate | 9.88 grams |
| lithium chloride | 0.6 gram |
| anhydrous cupric chloride | 3.9 grams |
| dimethylformamide | 155.4 mls. |
| acetic acid | 54.6 mls. |
| palladous chloride | 0.82 gram |

This mixture was heated to 100°C. in a reaction vessel equipped with a hollow-shafted cruciform stirrer, through which oxygen was passed at a rate of 20 liters per hour. n-Octene-1 (90 mls.) was then added and the reaction was carried out for 8 hours. At the end of this time, a further 30 mls. of n-octene-1 were added. After a total reaction time of 24 hours, during which 25 grams of octene had distilled off, the mixture was allowed to cool under a stream of oxygen. The product was extracted by pouring the solution into an equal volume of cold water, whereby an oil separated out. This oil was removed and bulked with a petroleum ether extract of the aqueous solution. After drying, this material containing petroleum ether was subjected to distillation, whereby three fractions were obtained:

| | |
|---|---|
| petroleum ether | 33.5 grams |
| octene | 22.3 grams |
| esters (90%) + octene (10%) | 21.1 grams |

Thus, the total weight of recovered octene was 49.4 grams, so that the weight of n-octene-1 which had not been accounted for was 36.6 grams. The yield of esters (19.0 grams) based upon this quantity of n-octene-1 was 34.8%. The ratio of primary to secondary esters was 1.9 : 1.

EXAMPLE 19

A reaction mixture was made up as follows:

| | |
|---|---|
| palladous chloride | 0.302 gram |
| lithium chloride | 0.312 gram |
| anhydrous lithium acetate | 3.301 grams |
| anhydrous cupric chloride | 1.302 grams |
| acetic acid | 15.6 mls. |
| dimethylformamide | 54.4 mls. |

This mixture was heated to 109°C., in a reaction vessel equipped with a hollow-shafted cruciform stirrer through which oxygen was blown at a rate of 20 liters per hour. n-Octene-1 (30 mls) was then added and the reaction was allowed to proceed for 5½ hours. The product was then poured into water and extracted with petroleum spirit. The extract was analysed spectroscopically and it was found that 8.5 grams of esters were present. Of these, 60% was primary ester. The amount of unreacted n-octene-1 was not determined so that the yield of esters can be expressed only upon the amount of octene fed. By calculating in this manner, it is found that the yield of esters is 26.2%, so that the yield of primary ester is 15.7%.

EXAMPLE 20

A reaction mixture was made up as follows:

| | |
|---|---|
| anhydrous lithium acetate | 3.306 grams |
| lithium chloride | 0.211 gram |
| anhydrous cupric chloride | 1.303 grams |
| acetamide | 43.62 grams |
| acetic acid | 16.36 grams |
| palladous chloride | 0.315 gram |

This mixture was heated to 110°C. in a reaction vessel equipped with a hollow-shafted cruciform stirrer through which oxygen was blown at 20 liters per hour. n-Octene-1 (21.6 grams) was then added and the reaction was carried out for 5 hours. The product was poured into water and extracted with petroleum spirit. The extract was made up to a standard volume and the amount of esters estimated spectroscopically. It was found that 9.5 grams of esters were present, this corresponding to a conversion to esters of 30% of the total amount of octene employed. Of the esters produced, 83% by weight was primary ester.

EXAMPLE 21

A reaction system was made up as follows:

| | |
|---|---|
| palladous chloride | 0.302 gram |
| lithium chloride | 0.333 gram |
| anhydrous lithium acetate | 3.299 grams |
| cuprous chloride | 1.301 grams |
| acetic acid | 15.6 mls. |
| dimethylacetamide | 44.6 mls. |

This mixture was heated to 104°C., in the presence of oxygen and n-octene-1 was introduced until 30 mls. had been added. The reaction was performed in a closed system, oxygen used up being replaced from a gas burette. Some carbon dioxide was formed and the concentration of this built up. After 2½ hours, it started to cause the precipitation of palladium. The reaction was terminated after 4 hours and the reaction product was poured into water and extracted with petroleum spirit. It was found that 8.0 grams of esters had been formed, 70% of this being primary ester. No attempt was made to determine the amount of unreacted n-octene-1 so that the yield of esters can only be expressed upon the quantity of n-octene-1 fed to the reaction. Calculation shows that 24.7% of this n-octene-1 had been converted to esters, the yield of primary ester based on the amount of n-octene-1 fed being 17.3%.

EXAMPLE 22

A solution was made up as follows:

| | |
|---|---|
| palladous chloride | 3.52 grams |
| lithium chloride | 1.67 grams |
| lithium acetate | 5.03 grams |
| cupric acetate | 21.6 grams |
| dimethylformamide | 150 mls. |
| acetic acid | 50 mls. |

Propylene was circulated for 135 minutes through the solution maintained at 105°–110°C. The product was collected in catchpots which were kept at −40°C. The volume of propylene absorbed was 542 mls., this corresponding to $2 \times 10^{-2}$ mole. The weight of the product obtained was 1.7 grams. This product had the following analysis:

| | |
|---|---|
| allyl acetate | 55% |
| isopropenyl acetate | 25% |
| acrolein | 5% |

-continued

| | |
|---|---|
| acetone | 15% |

Thus, the weight of ester obtained was 1.36 grams, this being a yield of 68% based on the amount of propylene absorbed. As will be seen, the ratio of primary to secondary ester was 55:25, i.e., 2.2:1. The acrolein and acetone are believed to have been formed by hydrolysis of the esters.

EXAMPLE 23

A solution of lithium acetate (5.0 grams), cupric acetate (21.6 grams), acetic acid (50 mls.) and dimethyl-formamide (150 mls.) was heated in a reactor to a temperature of 105°–110°C. The system was purged with butene-1 and a solution of palladous chloride (3.5 grams) and lithium chloride (1.7 grams) in acetic acid was then added. During the next 80 minutes, 650 mls. of butene-1 were absorbed. The reaction product was diluted with water and then extracted with petroleum ether. After the petroleum ether had been distilled off, there remained 2.4 grams of an oil which contained 1.2 grams of butenyl acetates. This corresponds to a yield of 38% of esters. The ratio of primary to secondary esters was found to be 3.9:1. The major product almost certainly had the structure $CH_3.CH=CH.CH_2.O.CO.CH_3$.

EXAMPLE 24

Four solutions were made up, each having the following composition:

| | |
|---|---|
| lithium acetate | 3.30 grams |
| lithium chloride | 0.20 gram |
| palladous chloride | 0.30 gram |
| acetic acid | 80 mls. |
| n-octene-1 | 10 mls. |

Further additions were made to each of the four solutions as follows:
  i. cupric acetate (2.4 grams)
  ii. cupric acetate (2.4 grams ) + benzonitrile (9.3 grams)
  iii. cupric acetate (2.4 grams) + dimethyl sulphoxide (10.1 grams)
  iv. cupric chloride (1.3 grams) + urea (6.0 grams)

Each mixture heated to 100°C., in a reaction vessel equipped with a hollow-shafted cruciform stirrer through which oxygen was passed at a rate of 20 liters per hour. At the end of the reaction period, the products were separated and the amounts of primary and secondary esters in the ester reaction product were measured. These results are given below.

| Additive | Primary Ester | Secondary Ester |
|---|---|---|
| none | 21% | 79% |
| benzonitrile | 37% | 63% |
| dimethyl sulphoxide | 54% | 46% |
| urea | 42% | 58% |

It will be observed that the three additives used in this Example all give a primary:secondary ester ratio which is greatly superior to that obtained in the absence of additives.

EXAMPLE 25

In this Example, the same quantities of palladous chloride, lithium acetate and cupric acetate were employed as in Example 10. Additionally there were present acetic acid (50 mls.) and dimethylformamide (150 mls.). As described in the preceding Examples, a mixture of oxygen and ethylene was passed through the reaction mixture which was maintained at a temperature of 104°C. A water-cooled reflux condenser was employed as in Example 2. The reaction was continued for 18 hours. On analysis, the following results were obtained:

| | |
|---|---|
| acetaldehyde | $3.2 \times 10^{-2}$ mole |
| ethylidene di-acetate | $0.54 \times 10^{-2}$ mole |
| vinyl acetate | $9.6 \times 10^{-2}$ mole |

From this Example, it will be observed that the presence of dimethylformamide gives a greatly enhanced ratio of vinyl acetate to ethylidene di-acetate.

EXAMPLE 26

Example 25 was repeated except that benzyl acetate was used in place of dimethylformamide, the volumes being the same. The reaction temperature was 120°C. and the reaction was continued for 23 hours. On analysis, the products were shown to include:

| | |
|---|---|
| acetaldehyde | $7.2 \times 10^{-2}$ mole |
| vinyl acetate | $7.3 \times 10^{-2}$ mole |
| ethylidene di-acetate | $0.4 \times 10^{-2}$ mole |

The presence of benzyl acetate, like that of dimethylformamide, enables a considerably enhanced vinyl acetate:ethylidene di-acetate ratio to be obtained.

EXAMPLE 27

A solution was made up as follows:

| | | |
|---|---|---|
| palladous chloride | 3.52 grams | $2 \times 10^{-2}$ mole |
| lithium chloride | 1.67 grams | $4 \times 10^{-2}$ mole |
| lithium acetate | 5.03 grams | $8 \times 10^{-2}$ mole |
| cupric acetate | 7.20 grams | $3 \times 10^{-2}$ mole |
| N,N-dimethylacetamide | 150 mls. | |
| acetic acid | 50 mls. | |

This solution was raised to a temperature of 105°C. and a gas mixture comprising 30% by volume ethylene and 70% by volume oxygen was passed through it at a rate of 10 liters per hour for 6 hours, a water-cooled reflux condenser being used. From the product, $9.55 \times 10^{-2}$ mole vinyl acetate and $0.65 \times 10^{-2}$ mole acetaldehyde were recovered. The quantity of di-esters was too small to be determined. It will be noted that the ratio of vinyl acetate to acetaldehyde obtained in this Example was 14.7:1.

EXAMPLE 28

Ethylene and oxygen were passed together through a solution of palladous chloride, lithium chloride, lithium acetate and cupric acetate in acetic acid. The reaction temperature was maintained at 104°C. The reaction was carried out under total reflux so that no water was removed from the reaction zone. The product consisting of acetaldehyde and esters had the molar composition 89.8% acetaldehyde, 5.9% ethylidene di-acetate, 4.0% vinyl acetate and 0.3% 1:2-diacetoxyethane.

A reaction was carried out under similar conditions using instead of acetic acid alone, a 3:1 volume mixture of dimethylformamide and acetic acid. The reaction was carried out using a water-cooled reflux condenser, so that only part of the water present in the reaction system was removed. The product consisting of acetaldehyde and esters had the molar composition 24% acetaldehyde, 4% ethylidene di-acetate and 72% vinyl acetate. These results show a small diminution in the amount of acetaldehyde formed under similar conditions but in the absence of dimethylformamide (24% as against 28.6%) and a large increase in the vinyl acetate:ethylidene di-acetate ratio (18:1 as against 0.13:1).

EXAMPLE 29

Two solutions were prepared in which the dimethylacetamide: acetic acid weight ratio was 3:1, while six solutions were prepared in which this ratio was 1:1. Each of these solutions had a volume of 200 ml. and contained:

| | |
|---|---|
| palladous chloride | 0.01 molar |
| lithium chloride | 0.5 molar |
| lithium acetate | 1.2 molar |
| cupric acetate | 0.4 molar |

Each of these solutions was raised to a temperature of 105°C. and a gas mixture comprising by volume 67% ethylene and 33% oxygen was passed through at a rate of 100 liters per liter of reaction mixture per hour. After 10 hours, the reaction product was analysed. The results obtained are presented in the Table below.

| Dimethyl acetamide: Acetic acid weight ratio | Final Water content % by weight | % Distribution of Products | | |
|---|---|---|---|---|
| | | Vinyl Acetate | Acetaldehyde | Ethylidene diacetate |
| 3:1 | 1.7 | 85 | 12.5 | 2.5 |
| 3:1 | 2.3 | 85 | 12.5 | 2.5 |
| 1:1 | 0.5 | 67 | 33 | 0 |
| 1:1 | 0.7 | 56 | 44 | 0 |
| 1:1 | 0.9 | 46 | 54 | 0 |
| 1:1 | 1.6 | 26 | 70 | 4 |
| 1:1 | 3.8 | 21 | 75 | 4 |
| 1:1 | 4.0 | 16.5 | 75.5 | 8 |

A repitition of the process described above using, however, acetic acid instead of a mixture of dimethylacetamide and acetic acid as the reaction medium gave the following molar percentage distribution of products: vinyl acetate, 8.0%; acetaldehyde, 68%; ethylidene diacetate, 24%.

EXAMPLE 30

In a mixture of acetic acid (21.5 grams), acetamide (55.5 grams) and n-octene-1 (22.0 grams) a solution was made up having the following composition:

| | |
|---|---|
| palladous chloride | 0.06 molar |
| lithium chloride | 0.07 molar |
| cupric chloride | 0.1 molar |
| cupric acetate | 0.28 molar |
| lithium acetate | 0.5 molar |

This solution was heated to 110°C. and oxygen was passed through it via a cruciform stirrer.

After the reaction had been carried out for 34 minutes, the product was analysed. The water content of the system at the end of the experiment was 1.8% by weight. The rates of ester and ketone formation were shown to have been 0.92 and 0.17 mole per liter per hour respectively. By weight, the product consisted of 82.5% primary octenyl acetate, 4.5% secondary esters and 13% mixed octanones.

EXAMPLE 31

Two solutions were made up, each consisting by volume of 25% acetic acid and 75% dimethylacetamide, and each of the following compounds in the concentration given:

| | |
|---|---|
| palladous chloride | 0.1 molar |
| lithium chloride | 0.2 molar |
| cupric acetate | 0.2 molar |
| lithium acetate | 0.4 molar |

These solutions were reacted, in the presence of oxygen, with butene-1 and butene-2 respectively. This was done by passing a mixture of equal volumes of the butene and oxygen into the catalyst solution at a rate of 50 liters per hour per liter of reaction mixture. The products were separated by extraction and distillation. The reaction was carried out for 4 hours at a temperature of 120°C. In each case, the rate of ester production was 0.03 moles per liter per hour. The final water content was in the region of 2% by weight. An analysis of the compounds produced in the two cases is given below, the amounts being molar percentages.

| | Using butene-1 | Using butene-2 |
|---|---|---|
| 3-acetoxy-butene-1 | 27 | 36 |
| 2-acetoxy-butene-1 | 2 | less than 1 |
| 2-acetoxy-butene-2 | 8 | 6 |
| 4-acetoxy-butene-1 | 15 | 0.5 |
| cis-1-acetoxy-butene-2 | 8 | 8 |
| trans-1-acetoxy-butene-2 | 40 | 49 |

EXAMPLE 32

In a solvent comprising by volume 50% acetic acid and 50% dimethylacetamide, a solution was made up as follows:

| | |
|---|---|
| palladous chloride | 0.028 molar |
| lithium chloride | 0.19 molar |
| lithium acetate | 1.5 molar |
| cupric acetate | 0.44 molar |

This solution was raised to a temperature of 100°C., and an ethylene-oxygen mixture was passed through it, the ethylene and oxygen partial pressures being 35 and 5 pounds per square inch gauge respectively. The final water content of the solution was 0.5% by weight. An analysis of the products indicated that the rates of vinyl acetate and acetaldehyde production were 0.08 and 0.03 mole per liter per hour respectively. No ethylidene di-acetate was detected.

EXAMPLE 33

Solutions were made up as follows in liquids consisting by volume of 25% acetic acid and 75% dimethylacetamide.

| | |
|---|---|
| Run No. 1 | |
| palladous chloride | 0.035 molar |
| lithium chloride | 0.07 molar |
| lithium acetate | 0.45 molar |
| cupric acetate | 0.28 molar |
| cupric chloride | 0.1 molar |
| Run No. 2 | |
| palladous chloride | 0.04 molar |
| lithium chloride | 0.4 molar |
| lithium acetate | 1.0 molar |
| cupric acetate | 0.45 molar |
| Runs Nos. 3 and 4 | |
| palladous chloride | 0.04 molar |
| lithium chloride | 0.4 molar |
| lithium acetate | 1.0 molar |
| cupric acetate | 0.45 molar |
| Run No. 5 | |
| palladous chloride | 0.04 molar |
| lithium chloride | 0.08 molar |
| lithium acetate | 1.0 molar |
| cupric acetate | 0.45 molar |

These solutions were raised to a temperature of 100°C. and reacted with a gas mixture comprising 90% by volume propylene and 10% by volume oxygen, the pressure in Runs No. 1 and 2 being 95 lbs. per square inch gauge and that in Runs No. 3, 4 and 5 being 250 lbs. per square inch gauge. An analysis of the results obtained is given in the table below.

| Run | Total amnt.of products (moles) | Production rate (moles/ltr/hr.) | Distribution of products (moles %) | | | | | | Final water content % by wt. |
|---|---|---|---|---|---|---|---|---|---|
| | | | acetone | acrolein | iso-propenyl acetate | allyl acetate | n-propenyl acetate | carbon dioxide | |
| 1 | 0.63 | 0.1 | 5.1 | 0 | 11.4 | 60.0 | 1.0 | 23.0 | 0.5 |
| 2 | 0.46 | 0.06 | 2.1 | 0 | 3.5 | 56.0 | 1.4 | 34.0 | 0.7 |
| 3 | 4.01 | 0.71 | 17.3 | 13.0 | 11.0 | 30.0 | 3.0 | 26.0 | 5.6 |
| 4 | 2.7 | 0.49 | 11.4 | 11.3 | 8.6 | 50.0 | 1.2 | 18.0 | 3.5 |
| 5 | 2.65 | 0.54 | 17.7 | 15.2 | 35.0 | 9.8 | 12.2 | 10.2 | 2.13 |

EXAMPLE 34

Solutions were made up in solvents as follows:
Run No. 1 — Acetic acid (200 mls.)
Run No. 2 — Acetic acid (50 mls.), dimethylacetamide (150 mls.)
Run No. 3 — Acetic acid (50 mls.), benzonitrile (150 mls.)
Run No. 4 — Acetic acid (33 mls.), sulpholane (100 mls.)
The following compounds were dissolved in each of these solutions to give the molar concentrations indicated:

| | |
|---|---|
| palladous chloride | 0.04 molar |
| lithium acetate | 1.00 molar |
| cupric acetate | 0.45 molar |

Reaction with each of these solutions was carried out as follows. The solution was raised to a temperature of 100°C., and propylene and oxygen were passed through, the rates of these being 10 and 5 liters per hour respectively. A cruciform stirrer was used to ensure thorough gas distribution throughout the liquid. The exit gas passed through a water-cooled condenser which returned condensed liquids to the reactor and then through cold traps maintained at −20°C. The duration of each of the runs and the products obtained (in moles × 1,000) is given in the table below. The final water content in each case was in region of 2%.

| Run No. | Time (hours) | allyl acetate | iso-propenyl acetate | n-propenyl acetate | acetone | 1:1 diacetoxy-propane | 1:2 diacetoxy-propane | 1:3 diacetoxy-propane |
|---|---|---|---|---|---|---|---|---|
| | | | | Products (moles × 1000) | | | | |
| 1 | 5 | 3 | 2 | 0.5 | 9 | 0.5 | 1 | 0 |
| 2 | 21 | 44 | 19 | 0 | 5 | 4 | 0 | 0 |
| 3 | 6 | 37 | 43 | 0 | 20 | 0 | 20 | 2 |
| 4 | 5 | 7 | 4 | 0.2 | 3 | 0 | 0 | 0 |

In the Table below, the percentage yields of these carbonyl and ester products are given, based upon the total amounts of these compounds formed.

| Run No. | allyl acetate | iso propenyl acetate | n-propenyl acetate | acetone | 1:1 diacetoxy-propane | 1:2 diacetoxy-propane | 1:3 diacetoxy-propane |
|---|---|---|---|---|---|---|---|
| | | | | % age yields | | | |
| 1 | 17 | 14 | 4 | 55 | 3 | 7 | 0 |
| 2 | 61 | 26 | 0 | 7 | 6 | 0 | 0 |
| 3 | 30 | 36 | 0 | 16 | 0 | 17 | 1 |
| 4 | 52 | 26 | 1 | 21 | 0 | 0 | 0 |

I claim:

1. A process for producing an ester of a carboxylic acid which comprises reacting in the liquid phase, an olefinically unsaturated hydrocarbon with a carboxylic acid in the presence of an alkali metal salt of a carboxylic acid, a palladous salt, a redox system and molecular oxygen under substantially anhydrous conditions.

2. A process for producing the unsaturated ester of a carboxylic acid which comprises reacting an olefinically unsaturated hydrocarbon with a carboxylic acid in the liquid phase in the presence of an alkali metal salt of a carboxylic acid, a palladous salt, a redox system and a minor amount of water allowing ester formation.

3. A process for producing the unsaturated ester of a carboxylic acid which comprises reacting an olefinically unsaturated hydrocarbon with a carboxylic acid in the liquid phase in the presence of an alkali metal salt of a carboxylic acid, a palladous salt, a metal salt redox system and a minor amount of water allowing ester formation.

4. A process for producing the unsaturated ester of a carboxylic acid which comprises reacting in the liquid phase, an olefinically unsaturated hydrocarbon with a carboxylic acid in the presence of an alkali metal salt of a carboxylic acid, a palladous salt, a metal salt redox system selected from the group consisting of copper and iron salts and a minor amount of water allowing ester formation.

5. A process as claimed in claim 2 in which the olefinic hydrocarbon is an α-olefine.

6. A process as claimed in claim 5 in which molecular oxygen is passed into the solution.

* * * * *